United States Patent
Wild et al.

(10) Patent No.: US 8,627,706 B2
(45) Date of Patent: Jan. 14, 2014

(54) GAS-MEASURING PROBE FOR DETERMINING THE PHYSICAL CHARACTERISTIC OF A MEASURING GAS

(71) Applicants: Bernhard Wild, Markgroeningen (DE); Rainer Maier, Tamm (DE); Gregor Jaehnig, Muehlacker (DE); Peter Dettling, Waiblingen (DE); Stefan Heinzelmann, Kernen (DE); Bernd Rattay, Ditzingen (DE); Bastian Buchholz, Stuttgart (DE); Juergen Moratz, Neuhausen (DE)

(72) Inventors: Bernhard Wild, Markgroeningen (DE); Rainer Maier, Tamm (DE); Gregor Jaehnig, Muehlacker (DE); Peter Dettling, Waiblingen (DE); Stefan Heinzelmann, Kernen (DE); Bernd Rattay, Ditzingen (DE); Bastian Buchholz, Stuttgart (DE); Juergen Moratz, Neuhausen (DE)

(73) Assignee: Robert Bosch GmbH, Stuttgart (DE)

( * ) Notice: Subject to any disclaimer, the term of this patent is extended or adjusted under 35 U.S.C. 154(b) by 0 days.

(21) Appl. No.: 13/788,190

(22) Filed: Mar. 7, 2013

(65) Prior Publication Data
US 2013/0186176 A1 Jul. 25, 2013

Related U.S. Application Data

(62) Division of application No. 11/404,234, filed on Apr. 13, 2006, now abandoned.

(30) Foreign Application Priority Data

May 4, 2005 (DE) .......................... 10 2005 020 793

(51) Int. Cl.
*G01N 31/00* (2006.01)
*G01N 7/00* (2006.01)

(52) U.S. Cl.
USPC .......................................... 73/31.05; 73/23.31

(58) Field of Classification Search
USPC .......... 73/23.2, 23.31, 23.32, 31.05; 439/471; 174/50.5; 277/607
See application file for complete search history.

(56) References Cited

U.S. PATENT DOCUMENTS

| 3,101,422 A | 8/1963 | Church et al. |
| 3,451,861 A * | 6/1969 | Norman et al. ............... 136/230 |
| 3,933,028 A | 1/1976 | Laud et al. |

(Continued)

FOREIGN PATENT DOCUMENTS

| DE | 196 11 572 | 9/1997 |
| WO | WO 9718610 | 5/1997 |

*Primary Examiner* — John Fitzgerald
(74) *Attorney, Agent, or Firm* — Kenyon & Kenyon LLP

(57) ABSTRACT

A gas-measuring probe for determining a physical characteristic of a measuring gas, in particular the concentration of a gas component or the temperature or pressure of the measuring gas, which includes a sensor element accommodated in a housing, at least one connection cable for the sensor element having an electrical conductor, which is enclosed by an insulation sheath and contacts the sensor element, and a cable channel sealing the housing end, which has at least one axial cable feedthrough through which the connection cable is guided out of the housing. To achieve long-lasting sealing at the cable-exit end of the housing even at higher temperatures, the insulation sheath of the connection cable is at least regionally welded to the cable wall of the cable feedthrough. To this end, a tube made of a material that fuses with the insulation sheath and the cable channel when heated is slipped over the cable section of the connection cable lying inside the cable channel.

10 Claims, 5 Drawing Sheets

(56) References Cited

U.S. PATENT DOCUMENTS

| | | | |
|---|---|---|---|
| 3,960,693 A * | 6/1976 | Weyl et al. | 204/428 |
| 4,187,163 A * | 2/1980 | Steinke et al. | 204/428 |
| 4,401,967 A | 8/1983 | Miwa et al. | |
| 4,560,463 A | 12/1985 | Frey et al. | |
| 4,897,174 A | 1/1990 | Wang et al. | |
| 5,121,461 A | 6/1992 | Yamamoto et al. | |
| 5,874,664 A * | 2/1999 | Watanabe et al. | 73/23.32 |
| 5,948,963 A | 9/1999 | Kato et al. | |
| 5,949,023 A * | 9/1999 | Weyl | 174/77 R |
| 6,178,806 B1 * | 1/2001 | Watanabe et al. | 73/23.32 |
| 6,246,000 B1 | 6/2001 | Wehrmann et al. | |
| 6,658,918 B2 * | 12/2003 | Hibino et al. | 73/31.05 |
| 7,066,009 B2 * | 6/2006 | Yamada | 73/31.05 |
| 7,124,623 B2 * | 10/2006 | Nakagawa | 73/23.31 |
| 7,399,925 B2 * | 7/2008 | Yamauchi | 174/74 R |
| 2001/0025522 A1 | 10/2001 | Kojima | |
| 2003/0074950 A1 | 4/2003 | Yamada et al. | |
| 2004/0244467 A1 | 12/2004 | Yamada | |
| 2005/0132778 A1 | 6/2005 | Nakagawa | |
| 2006/0162422 A1 | 7/2006 | Geier et al. | |
| 2007/0033986 A1 * | 2/2007 | Wild et al. | 73/31.05 |
| 2007/0056353 A1 | 3/2007 | Weyl et al. | |
| 2007/0101801 A1 * | 5/2007 | Yamauchi | 73/23.32 |
| 2007/0113617 A1 * | 5/2007 | Yamauchi | 73/31.05 |
| 2007/0175267 A1 * | 8/2007 | Yamauchi et al. | 73/31.05 |

* cited by examiner

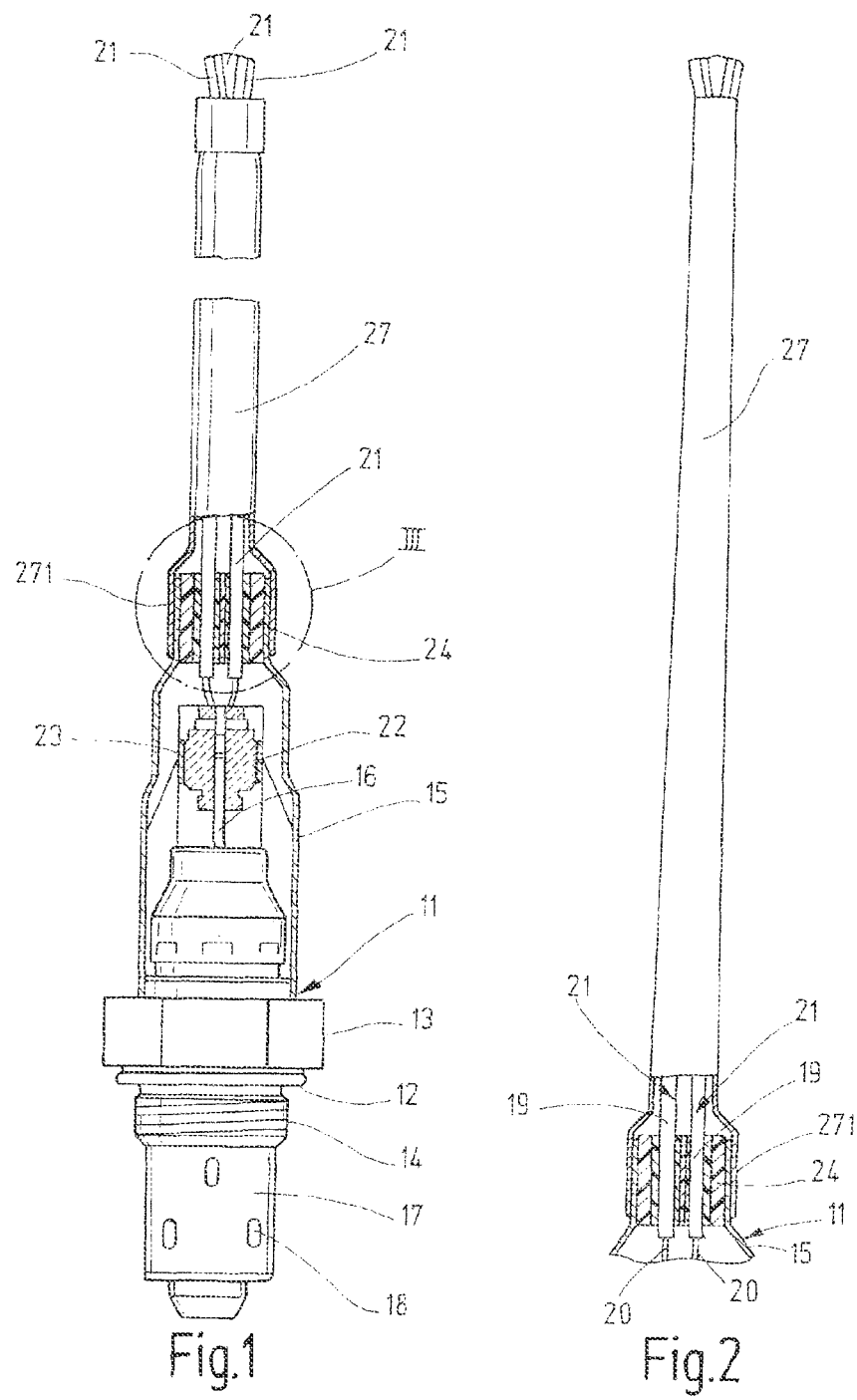

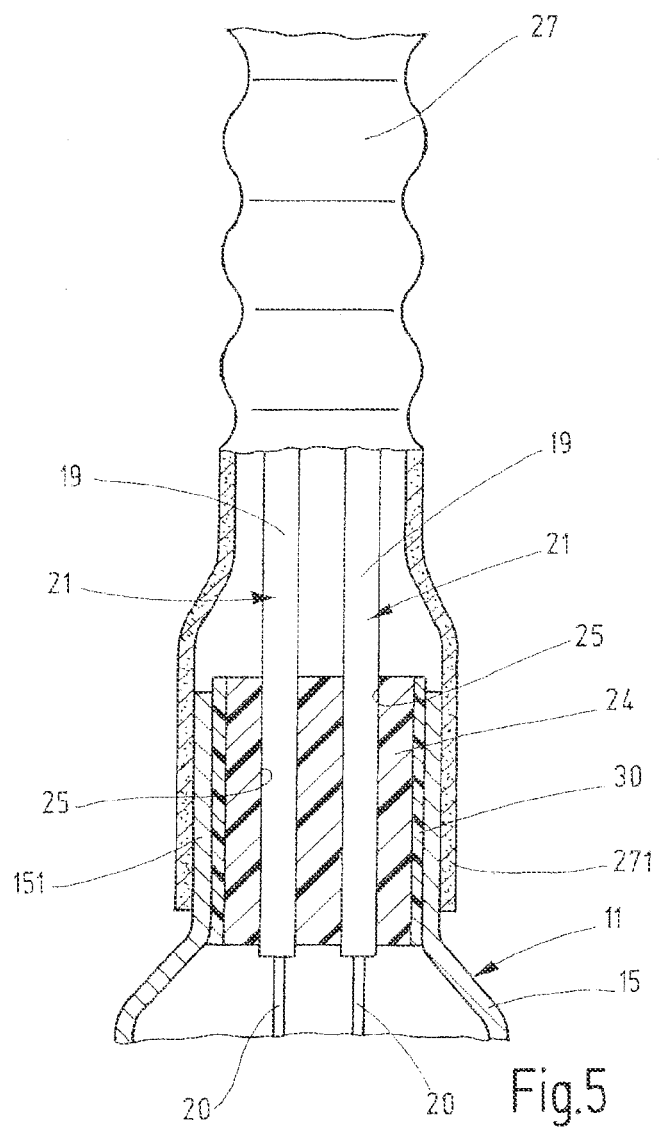

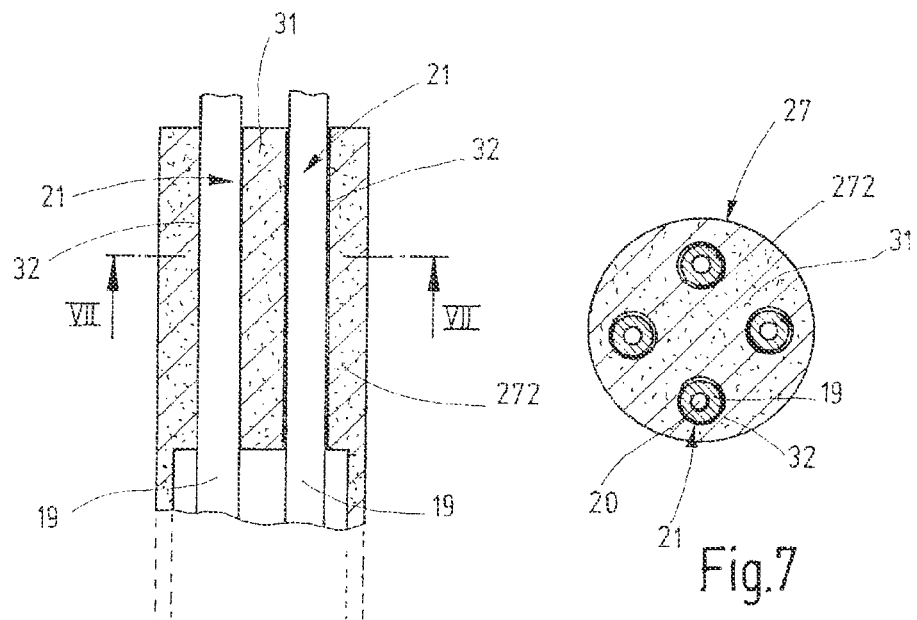
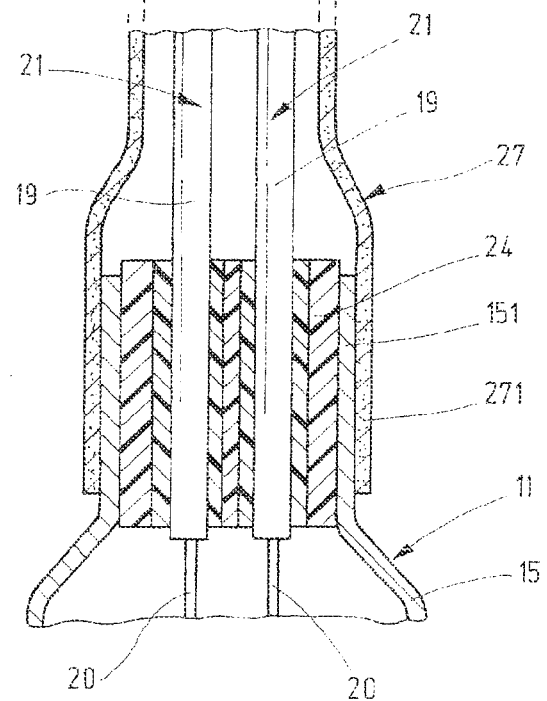

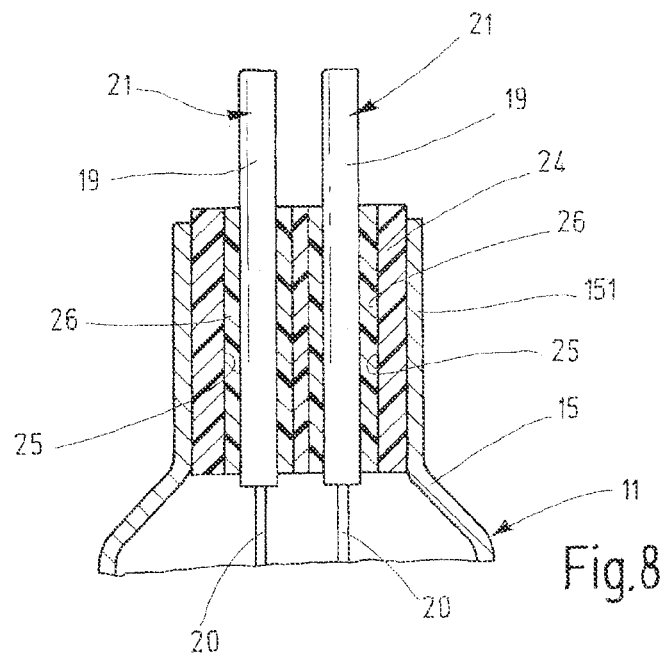
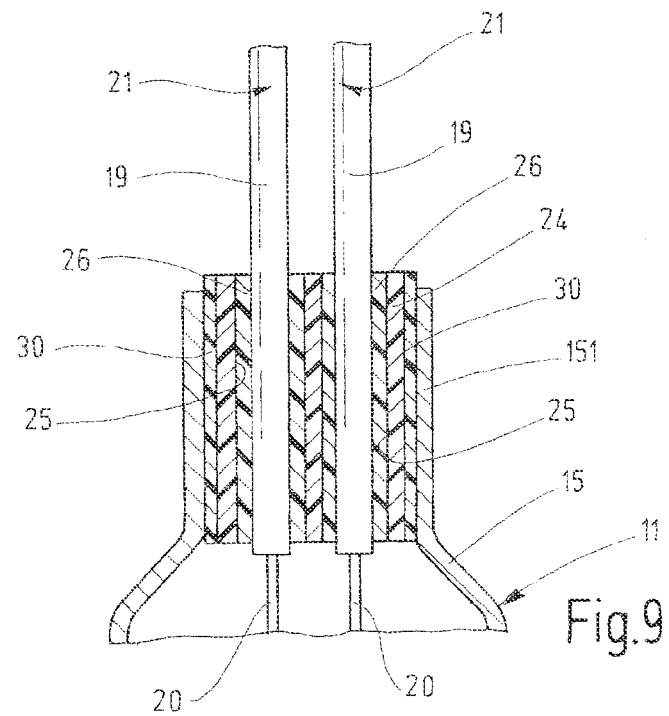

GAS-MEASURING PROBE FOR DETERMINING THE PHYSICAL CHARACTERISTIC OF A MEASURING GAS

CROSS-REFERENCE TO RELATED APPLICATIONS

The present application is a divisional application of U.S. patent application Ser. No. 11/404,234, filed on Apr. 13, 2006, which claims priority to German Patent Application No. 102005020793.6, filed on May 4, 2005, the contents of all of which are hereby incorporated by reference in their entireties.

FIELD OF THE INVENTION

The present invention relates to a gas-measuring probe for determining the physical characteristic of a measuring gas, in particular the concentration of a gas component or the temperature or pressure of the measuring gas.

BACKGROUND INFORMATION

In a known measuring-gas probe (German Patent Application No. DE 196 11 572), the connection cables, which are electrically and mechanically connected to contact surfaces on the sensor element, are accommodated in a cable sheathing at the end of the cable feedthrough, the sheathing being made up of an at least sectionally porous PTFE tube. The PTFE tube is slipped over a reduced-diameter housing section of the housing on the end side and shrink-fitted onto the housing section by heating. Reference air from the environment can penetrate the housing through the porous PTFE hose, the PTFE hose simultaneously preventing moisture or impurities from getting inside the housing.

SUMMARY OF THE INVENTION

The gas-measuring probe according to the present invention has the advantage that reliable sealing is achieved at the cable exit point of the housing even at higher temperatures so that improved temperature resistance of the gas-measuring probe is ensured. Moreover, high resistance against the cable being pulled out of the housing is achieved, so that damage during the installation by severing of the electrical contact connections between the connection cable and sensor element, which may render the gas-measuring probe useless, is reliably prevented.

According to an advantageous specific embodiment of the present invention, the preferably several connection cables run in a shared shrink tube, at least at the housing exit, the shrink tube having been shrink-fitted onto the housing via an end section of the tube. Owing to the shrink tube, the sealing-tightness at the cable exit point is improved further and the thermal loading of the connection cables guided in the shrink tube is reduced as well.

If the shrink tube is dyed or pigmented according to an advantageous specific embodiment of the present invention, this may be utilized to adjust the emission degree of the tube material and to suppress the introduction of heat into the shrink tube even further. The same is achieved if the shrink tube is made of a plurality of layers.

According to an advantageous specific embodiment of the present invention, the shrink tube has at least one tube section made of solid material in which axial feedthrough ducts for the preferably several connection cables are present. The tube section made of a solid material preferably lies at the tube end that faces away from the housing. In conjunction with the cable feedthrough situated at the housing exit, the connection cables are thus guided in the shrink tube in a defined manner and the cable ends emerging from the shrink tube at the housing-remote end of the shrink tube are able to be fitted more easily on the plug side.

BRIEF DESCRIPTION OF THE DRAWING

FIG. 1 shows a side view of a gas-measuring probe in a part-sectional view.

FIG. 2 shows a representation, identical to FIG. 1, of a modified gas-measuring probe in a cutaway view.

FIG. 5 shows a partial longitudinal section of a gas-measuring probe according to an additional exemplary embodiment in a cutaway view.

FIG. 6 shows a longitudinal section of a gas-measuring probe according to an additional exemplary embodiment in a cutaway view.

FIG. 7 shows a section along line VII-VII in FIG. 6.

FIGS. 8 and 9 show longitudinal sections of a gas-measuring probe according to an additional exemplary embodiment in a cutaway view.

DETAILED DESCRIPTION

Figure 3:
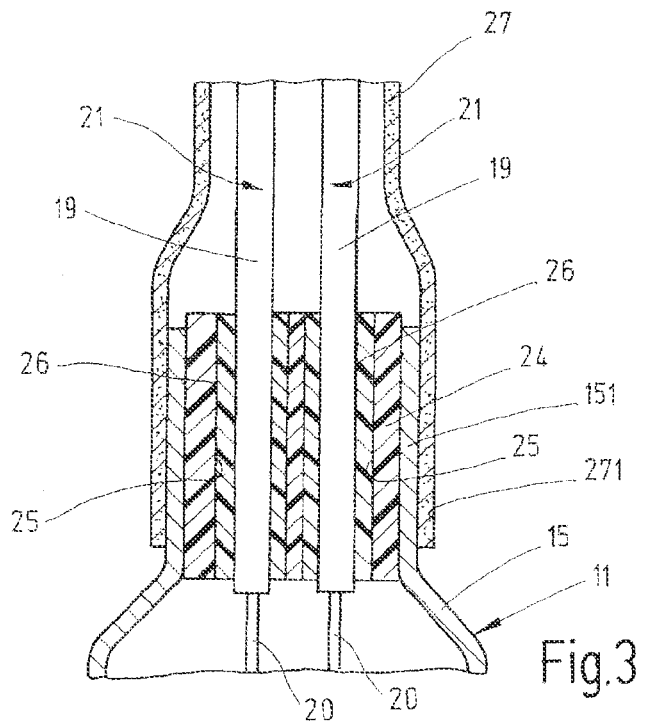
FIG. 3 shows an enlarged view of cutout III in FIG. 1.

The gas-measuring probe shown in a side view and in a part-sectional view in FIG. 1 by way of example is configured as a lambda probe for measuring the oxygen concentration in the exhaust gas of internal combustion engines. However, it may also be designed as a temperature probe or as a pressure measuring device or as a sensor for measuring the nitrogen-oxide concentration in the exhaust gas. The gas-measuring probe has a housing 11, which is made up of a massive hollow housing body 12 made of metal having a screw thread 14 and an installation hex bolt 13 for screwing housing body 12 into a connection piece situated on the exhaust-gas pipe of an internal combustion engine, as well as a protective sleeve 15 slipped over housing body 12 and permanently joined thereto, the protective sleeve having a housing-remote end section 151 whose diameter is reduced. Situated in housing 11 is a sensor element 16, which projects from housing 11 by a measuring-gas-side end and is covered there by a protective tube 17, which has gas-exit holes 18 and is fixed in place on housing body 12. At the connection-side end, which faces away from the end on the measuring-gas-side, sensor element 16 has contact surfaces, which are connected (not shown further here) via circuit traces to measuring electrodes situated at the end on the measuring-gas side. Electrical conductors 20, enclosed by insulation sheath 19, of connection cables 21 are contacted at the contact surfaces. In the exemplary embodiment, a two-part ceramic clamping body 22 is provided for the contacting of contact surfaces and electrical conductors 20; on the outside clamping body 22 is surrounded by a spring element 23 and presses electrical conductors 20 onto the contact surfaces of sensor element 16 by force-locking. Ceramic clamping body 22 is radially supported at protective sleeve 15.

A cable feedthrough made of a fluorine-containing plastic such as PTFE is inserted in diameter-reduced end section 151 of protective sleeve 15, the cable feedthrough having a number of axial cable feedthroughs 25 that corresponds to the number of connection cables 21. Connection cables 21, which are fixed in place on sensor element 16 by force-locking via their electrical conductors 20, are fed through cable feedthroughs 25 and emerge from protective sleeve 15 at the end of cable channel 24. In order to achieve adequate sealing at the cable exit even at higher temperatures, insulation sheath 19 of connection cables 21 made of fluorine-containing material is at least regionally welded to the channel wall of cable feedthroughs 25. As can be gathered from the enlarged cutaway view of FIG. 3, the inside diameter of cable feedthroughs 25 in the exemplary embodiment of FIG. 1 is larger dimensioned than the outer diameter of connection cables 21. A welding tube 26 made of a fluorine-containing plastic is slipped over the cable sections lying within cable feedthroughs 25, the welding tube together with the particular connection cable 21 being threaded into associated cable feedthrough 25 of cable channel 24. When suitably heated, welding tube 26 fuses with the material of insulation sheath 19 on the one hand and with the material of cable channel 24 on the other hand, so that both high sealing of the cable exit point and also high resistance with respect to the cable being pulled out of housing 11 is produced.

From the point of exit from the housing, connection cables 21 are accommodated in a shared shrink tube 27, which is slipped over end section 151 of protective sleeve 15 via its tube end section 271 on the side of the housing. By preheating shrink tube 27 or end section 151 of protective sleeve 15, shrink tube 27 shrinks and is pressed onto end section 151 in a sealing manner. Shrink tube 27 may have one or a plurality of layers and is made of a material which has mechanical, physical and chemical properties that are comparable to fluorine-containing plastics.

For instance, shrink tube 27 is made of polyolefin vulcanized by high-energy radiation. Shrink tube 27 is elastically deformable; the material hardness of shrink tube 27 is able to be adjusted in such a way that connection cables 21 guided in shrink tube 27 are not bent. The form of shrink tube 27 is variable. In the exemplary embodiment of FIG. 1, shrink tube 27 has an approximately constant inside diameter across its length enclosing connection cables 21. In the exemplary embodiment of FIG. 2, the inside diameter of shrink tube 27 tapers from the end on the housing side to the end on the plug side. The tapering is continuous, but may also be implemented in steps. In the exemplary embodiment of FIG. 5, shrink tube 27 is implemented as a corrugated tube so as to simplify the installation in the installation space of the gas-measuring probe. Shrink tube 27 is dyed or color-pigmented, which allows the emission degree of the tube material to be adjusted and a high emission degree to be achieved so that little heat is introduced into the tube interior and connection cables 21 are protected from excessive temperature loads.

Figure 4:
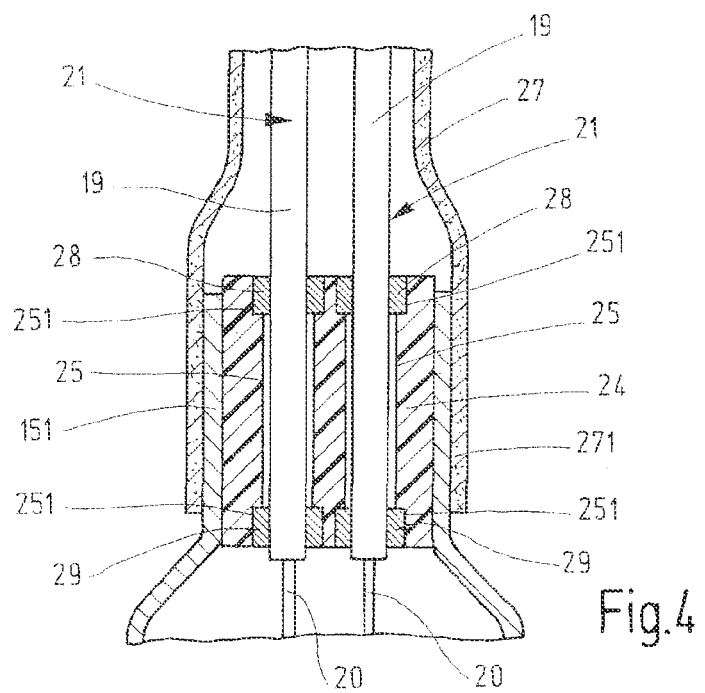
FIG. 4 shows a representation, identical to FIG. 3, of a variant of an embodiment of the gas-measuring probe.

In the modified gas-measuring probe illustrated in a cutaway view in FIG. 4, the welding between connection cable 21 and cable channel 24 is not implemented across the entire length of cable feedthroughs 25, but only at the entry and exit points of connection cables 21 into or out of cable channels 24. For this purpose, cable feedthroughs 25 have channel sections 251 having a larger diameter at both channel ends. After connection cables 21 have been threaded through cable feedthroughs 25, a welding mass 28 made of a fluorine-containing material is introduced into channel sections 251, which, when adequately heated, fuses with insulation sheaths 19 of connection cables 21 and the bore walls of cable feedthroughs 25 in cable channel 24. Instead of welding mass 28, welding rings 29 made of the same material may be used as well, which are slipped over connection cables 21. Following alignment of connection cables 21 within cable feedthroughs 25 of cable channel 24, welding rings 29 are inserted into the diameter-enlarged channel sections 251 at the end faces of cable channels 24 and heated again to fuse with the material of insulation sheath 19 and cable channel 24. For a simplified illustration, FIG. 4 shows welding mass 28 in upper channel section 251 and a welding ring 29 in lower channel section 251.

In the exemplary embodiment of FIG. 5, a tube 30 made of fluorine-containing plastic is slipped over cable channel 24 for improved sealing between cable channel 24 and protective sleeve 15. By suitable heating, tube 30 is pressed onto cable channel 24 and seals cable channel 24 across its length with respect to end section 151 of protective sleeve 15 as well.

The additional exemplary embodiment of the gas-measuring probe shown in FIG. 6 in a cutaway view differs from the gas-measuring probe described in connection with FIGS. 1 and 3 only in that shrink tube 27 has in the housing-remote end region a tube section 272 made of solid material 31. The solid material has axial feedthrough channels 32 for connection cables 21 whose number corresponds to the number of connection cables 21 guided in shrink tube 27 (FIG. 7). Shrink tube 27 having tube section 272 made of a solid material is designed in one piece.

The exemplary embodiments of the gas-measuring probe illustrated in FIGS. 8 and 9 differ from the afore-described exemplary embodiments in that shrink tube 27 has been omitted and the sealing of housing 11 on the side of the cables is achieved exclusively by the described welding tubes 26 on connection cables 21. In the exemplary embodiment of FIG. 9, additional sealing of cable channel 24 with respect to protective sleeve 15 of housing 11 has been implemented with the aid of a tube 30 made of fluorine-containing material, as it is described in connection with FIG. 5.

Of course, it is possible to use welding mass 28 or welding ring 29 described in FIG. 4 instead of welding tubes 26, and to place them in channel sections having a larger diameter in the end faces of cable channel 24 in order to then fuse them with insulation sheaths 19 of connection cables 21 and cable channel 24.

What is claimed is:

1. A gas-measuring probe for determining a physical characteristic of a measuring gas, comprising:
   a housing;
   a sensor element accommodated in the housing;
   at least one connection cable for the sensor element, which has an electrical conductor enclosed by an insulation sheath and contacts the sensor element; and
   a cable channel sealing a housing end, which has at least one axial cable feedthrough through which the at least one connection cable is guided out of the housing,
   wherein the insulation sheath of the connection cable is at least regionally welded to a channel wall of the cable feedthrough in the cable channel, wherein the at least one cable feedthrough has, at at least one channel end, a channel section having a larger inside diameter, which, after the connection cable has been threaded through the cable feedthrough, is filled with a material that fuses with the insulation sheath and the channel wall of the cable feedthrough in the cable channel after heating.

2. The gas-measuring probe according to claim 1, wherein a welding point is situated at at least one of an entry and an exit point, at least one of into and out of the cable channel of the at least one connection cable.

3. The gas-measuring probe according to claim 1, wherein the insulation sheath of the connection cable, the cable channel and a material for fusing with the insulation sheath and the cable channel are composed of fluorine-containing plastic.

4. The gas-measuring probe according to claim 1, wherein the at least one connection cable includes a plurality of connection cables which are electrically connected to the sensor element and are guided out of the housing, and the cable channel has a number of cable feedthroughs that corresponds to a number of connection cables.

5. The gas-measuring probe according to claim 1, wherein the probe determines at least one of (a) a concentration of a gas component, (b) a temperature of the measuring gas, and (c) a pressure of the measuring gas.

6. The gas-measuring probe according to claim 1, wherein, at least at a housing exit, the at least one connection cable extends in an interior of a shrink tube, which is shrink-fitted onto the housing via one tube end section.

7. The gas-measuring probe according to claim 6, wherein the shrink tube is bendable.

8. The gas-measuring probe according to claim 6, wherein the shrink tube tapers in one of a continuous and a stepped manner in a direction of a housing-remote end.

9. The gas-measuring probe according to claim 6, wherein the shrink tube is one of dyed and color-pigmented.

10. The gas-measuring probe according to claim 6, wherein the shrink tube has at least one layer.

* * * * *